United States Patent [19]

Nadaud et al.

[11] Patent Number: 5,567,426
[45] Date of Patent: Oct. 22, 1996

[54] COSMETIC COMPOSITON IN THE FORM OF A GELLED TRIPLE WATER/SILICONE OIL/WATER EMULSION

[75] Inventors: Jean F. Nadaud, Paris; Laurence Sebillotte, Creteil, both of France

[73] Assignee: L'Oreal, Paris, France

[21] Appl. No.: 367,244

[22] PCT Filed: Jun. 30, 1993

[86] PCT No.: PCT/FR93/00658

§ 371 Date: Jan. 6, 1995

§ 102(e) Date: Jan. 6, 1995

[87] PCT Pub. No.: WO94/01073

PCT Pub. Date: Jan. 20, 1994

[30] Foreign Application Priority Data

Jul. 9, 1992 [FR] France ................................. 92 08532

[51] Int. Cl.$^6$ ........................................................ A61K 7/06
[52] U.S. Cl. ...................... 424/401; 524/501; 424/70.12; 424/78.03
[58] Field of Search ................................ 424/401, 70.12, 424/78.03; 524/501

[56] References Cited

U.S. PATENT DOCUMENTS 4,960,764 10/1990 Figueroa, Jr. et al. .................. 514/63
5,306,498 4/1994 Vesperini et al. ...................... 424/401

FOREIGN PATENT DOCUMENTS

| 0281394 | 9/1988 | European Pat. Off. . |
| 0330369 | 8/1989 | European Pat. Off. . |
| 0345075 | 12/1989 | European Pat. Off. . |
| 0391124 | 10/1990 | European Pat. Off. . |
| 0422984 | 4/1991 | European Pat. Off. . |
| 2670673 | 6/1992 | France . |
| 2242358 | 10/1991 | United Kingdom . |

*Primary Examiner*—Mark D. Sweet
*Attorney, Agent, or Firm*—Cushman Darby & Cushman, L.L.P.

[57] ABSTRACT

A gelled silicone/water triple water/oil emulsion comprises (A) a gelled continuous external aqueous phase containing at least a $C_3$–$C_6$ monoethylene carboxylic acid anhydride or acid/fatty chain acrylic ester copolymer type fatty chain gelling agent, and (B) a silicone fatty phase comprising at least the silicone oil and a silicone emulsifier, forming a primary W/O emulsion with an aqueous phase. The triple emulsion disclosed may be used as a base for cosmetic or dermatologically active compositions for use on the skin or hair.

20 Claims, No Drawings

COSMETIC COMPOSITON IN THE FORM OF A GELLED TRIPLE WATER/SILICONE OIL/WATER EMULSION

The present invention relates to a cosmetic or dermatological composition which is in the form of a gelled triple water/silicone oil/water emulsion, to the process for its preparation and to its applications in the cosmetic field.

For many years emulsions have been used in products for cosmetic treatment of the skin, especially in the field of cosmetics. These emulsions are generally oil-in-water (O/W) or water-in-oil (W/O) emulsions.

Triple emulsions of the W/O/W or else the O/W/O type are also used in cosmetics or dermatology. However, such emulsions are subject to numerous problems during their production, or else to problems of stability over time, and in particular when active substances which may have a tendency to destabilize the prepared emulsions are introduced into these emulsions.

Patent Application EP-A-0 345 075 (UNILEVER) describes triple W/O/W emulsions in which the continuous external phase is gelled and which contain an osmotic pressure agent in the internal aqueous phase, this agent drawing the water from the external phase through the oily phase. The process for the preparation of these gelled emulsions consists in dispersing a water-in-oil emulsion, in which the aqueous phase contains an osmotic pressure agent, in a solution of a gelling agent of the polysaccharide, gelatin or other protein type. These emulsions, however, have disadvantages. The difference in osmotic pressure between the internal aqueous phase and the external aqueous phase brings about an escape of water from the external aqueous phase to the internal aqueous phase, and therefore a swelling of the internal aqueous globules, and a high concentration of gelling agent in the external aqueous phase, leading ultimately to an excessively gelatinous product.

Patent Application EP-A-0 281 394 (RICHARDSON VICKS) relates to a O/W/silicone emulsion. This is a very specific emulsion obtained by introducing a conventional O/W emulsion into a silicone-containing oily phase which constitutes the outer oily phase. This emulsion contains various surfactants which act as emulsifiers in the O/W emulsion.

However, it is known that the use of a large quantity of surfactants in an emulsion for cosmetic use may cause skin reactions of the allergic or irritative type.

It is therefore necessary to seek to minimize the quantities of surfactants, while not destabilizing the emulsion.

It is also known that the conventional oils used in the emulsions impart a greasy feel and are often comedogenic. The Applicant has therefore sought to replace these conventional oils with oils which do not impart a greasy feel and which, moreover, guarantee appropriate moisturizing of the skin.

The applicant has succeeded in overcoming the difficulties, both technical and cosmetic, which are connected with the triple emulsions of the prior art, and in obtaining a triple emulsion which has an appearance and a feel which are completely original, as well as noteworthy stability properties.

The triple emulsion according to the invention is a gelled water/silicone oil/water (W/Si/W) emulsion in which the primary water/silicone oil emulsion is distributed homogeneously with globules of a size between 0.5 and 50 μm, giving it a smooth and shiny appearance. The triple emulsion according to the invention is in addition gelled, translucent, unctuous, fresh, soft, non-greasy and stable.

One subject of the invention is therefore a triple emulsion which has the characteristics defined below.

Another subject of the invention consists of the process for the preparation of such an emulsion.

Yet another subject of the invention is the cosmetic or dermatological use of such an emulsion.

Other subjects of the invention will become evident on reading the description and the examples which follow.

The gelled triple water/silicone oil/water emulsion according to the invention is essentially characterized in that it comprises (A) a gelled, continuous, external aqueous phase which comprises at least one fatty-chain gelling agent of the $C_3$–$C_6$ monoethylenic carboxylic acid or anhydride/fatty-chain acrylic ester copolymer type; and (B) a silicone-containing fatty phase comprising at least one silicone oil and a silicone-containing emulsifier, forming the primary W/O emulsion with an aqueous phase.

The gelled, continuous, external aqueous phase of the triple W/O/W emulsion according to the invention comprises water and a fatty-chain gelling agent of the type which is a copolymer of a monoethylenic carboxylic acid containing 3 to 6 carbon atoms (or its anhydride) and of a long-chain acrylic ester.

This type of water-soluble acrylic copolymer, which may be crosslinked and which will be referred to below as "fatty-chain gelling agent", is described in EP-A-0 268 164. In this copolymer, the proportion of monomeric acid is preferably from 90 to 98% by weight and the proportion of monomeric ester is preferably from 10 to 2% by weight.

The monomeric acid has the formula:

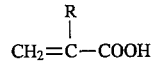

in which formula R represents H, a halogen, OH, a lactone or lactam radical, a group —C≡N, or a $C_1$–$C_3$ alkyl radical. The preferred monomers are acrylic acid and maleic anhydride.

The monomeric ester has the formula:

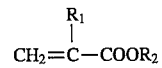

in which formula:
$R_1$ is H, methyl or ethyl, and
$R_2$ is a $C_8$–$C_{30}$ alkyl radical or a $C_8$–$C_{30}$ oxyalkylene radical. $C_{10}$–$C_{22}$ alkyl radicals are preferred. Preferred monomeric esters which may be mentioned include: decyl, lauryl, stearyl, behenyl and melissyl acrylates and methacrylates.

The copolymers used in accordance with the invention are, at least in some cases, distributed commercially; they are, for example, marketed under the names PEMULEN and CARBOPOL 1342 by the company GOODRICH.

The gelled, continuous, external aqueous phase may additionally comprise other constituents, such as other gelling agents of the carboxyvinyl polymer type, for instance those sold under the names CARBOPOL 980 or 942 or 950, etc., by the company GOODRICH or that sold under the name SYNTHALENK by the company SIGMA, glyceryl polymethacrylates sold by the company GUARDIAN under the name LUBRAJEL MS, carragheenans such as the product sold by the company SANOFI under the name SATIAGEL K80 (D. Galactopyrannose [sic] sulphate), xanthan gums such as the xanthane/polysaccharides product containing glucose/mannose/glucuronic acid units (40/30/30) and sold by the company KELCO under the name KELTROL.

The external aqueous phase may also contain glycols and neutralizing agents such as triethanolamine or sodium hydroxide. It may also contain preservatives, dyes, fragrances, active agents, sunscreens, moisturizing agents such as glycerine, unctuosity agents such as the product SEPIGEL 305 (neutralized 2-acrylamido-2-methylpropanesulphonic acid/acrylamide crosslinked copolymer) sold by the company SEPPIC.

The primary water-in-oil (W/O) emulsion comprises a silicone-containing fatty phase and an aqueous phase.

The silicone-containing fatty phase consists essentially of at least one silicone-containing emulsifier and a silicone oil. It may additionally comprise a thickener chosen from silicone resins, gums or waxes, and, if appropriate, nonsilicone-containing oils.

The silicone-containing emulsifiers which are present in the primary W/O emulsion according to the invention may be chosen from dimethicone copolyols and, preferably, the alkyl dimethicone copolyols of the general formula:

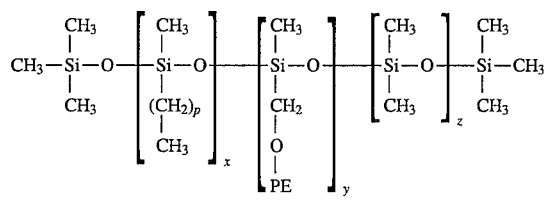

in which:
p is an integer between 7 and 17
x is an integer between 1 and 100
y is an integer between 1 and 40
z is an integer between 0 and 200
PE=$(C_2H_4O)_a$—$(C_3H_6O)_b$—H of molecular weight between 250 and 2000;
a and b are chosen such that the ratio by weight of the groups $C_2H_4O/C_3H_6O$ is between 100:0 and 20:80.

It is possible in particular to use the products sold under the names ABIL WE 09, ABIL EM 90 by the company GOLDSCHMIDT, Q2 3225 C by the company DOW CORNING and 218-1138 by the company RHONE POULENC.

The silicone oils which are present in the primary emulsion and may be used according to the invention may be chosen from:

a) the cyclomethicones of general formula:

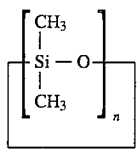

in which n is an integer between 3 and 8.

Particularly preferred cyclomethicones which can be mentioned include cyclotetradimethylsiloxane (n=4), cyclopentadimethylsiloxane (n=5) and cyclohexadimethylsiloxane (n=6).

It is possible in particular to use the products sold by the company DOW CORNING under the names DC FLUID 4, DC FLUID 245, DC FLUID 344 and DC FLUID 345.

Other cyclomethicones which can be used according to the invention are those sold by the company GOLDSCHMIDT under the name ABIL K04, by the company RHONE POULENC under the names SILBIONE 70045 V2 and SILBIONE HUILE 70045 V5, as well as by the company UNION CARBIDE under the names VOLATIL SILICONE 7158 and VOLATIL SILICONE 7207;

b) the polydimethylsiloxanes (DIMETHICONES) of general formula:

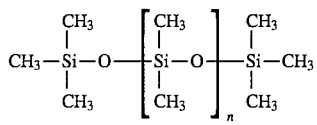

in which, when n<3, a volatile dimethicone is present, when 3<n<2000, the viscosity of the dimethicone is between $1.5 \times 10^{-6}$ m$^2$/s and $2.5 \times 10^{-1}$ m$^2$/s.

The polydimethylsiloxanes which are commercially available and can be used in the present invention include:

DC FLUID 200 (of a viscosity between $10^{-6}$ m$^2$/s and $2.5 \times 10^{-3}$ m$^2$/s sold by the company DOW CORNING, ABIL 10 and ABIL K03 sold by the company GOLDSCHMIDT, RHODORSIL 47 V 10, SILBIONE 70047 V 10, SILBIONE 70047 V 100, SILBIONE 70047 V 300 sold by the company RHONE POULENC, and SILICONE OIL L45 ($10^{-5}$–$10^{-4}$ m$^2$/s) sold by the company UNION CARBIDE;

c) the polyphenyltrimethylsiloxanes (PHENYLTRIMETHICONES) of general formula:

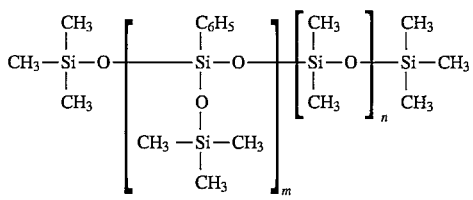

in which:
n is an integer between 0 and 100, and
m is an integer between 1 and 400.

The compounds which can be used according to the invention and may be mentioned include the following commercial products: ABIL AV 200 and ABIL AV 1000 sold by the company GOLDSCHMIDT;

d) the trimethylsilyl monopentaerythritol of formula:

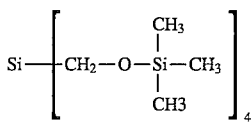

which forms part of the composition of the product sold under the name HUILE CL 1680 by the company RHONE POULENC;

e) fluorinated silicones, in particular polydimethylsiloxanes grafted with trifluoroalkyl groups, of general formula:

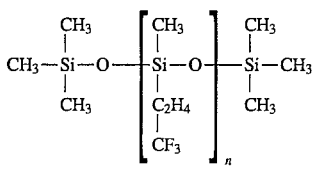

in which n is an integer between 1 and 300, and more particularly those sold under the names X22-819, X22-820, X22-821, X22-822, FL-100/450 by the company SHIN ETSU.

The silicone gums which can be used in the primary emulsion of the present invention may be chosen from:

the polydimethylsiloxanes (DIMETHICONES) of high molecular weight and of the general formula indicated above, in which n>2000, such as the product sold under the name VISCASIL 60M sold [sic] by the company GENERAL ELECTRIC;

the polydimethylsiloxane-OLs (DIMETHICONE-OLs) of general formula:

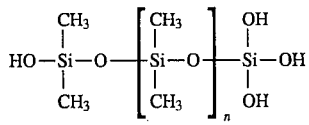

in which n > 2000, among which the following commercial products may be mentioned:

DC SGM-3, Q2-1403 ($10^{-4}$ $m^2$/s) and DC QC F2-1671, sold by the company DOW CORNING.

The silicone waxes which can be used in the primary emulsion according to the present invention include:

alkoxypolydimethylsiloxanes (ALKOXY DIMETHICONES) of general formula:

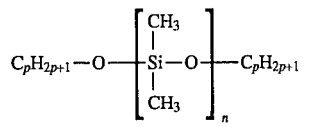

in which:
p is an integer ranging from 3 to 30,
n is an integer ranging from i to 200.

More particularly it is possible to mention the stearoxypolydimethylsiloxanes sold under the name ABIL WAX 2434 by the company GOLDSCHMIDT and DC 580 sold by the company DOW CORNING;

alkylpolysiloxanes (ALKYL DIMETHICONES) of general formula:

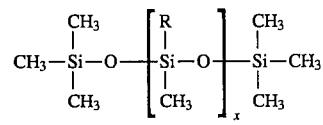

in which:
R represents $C_nH_{2n+1}$ where n is an integer ranging from 16 to 30,
x is an integer ranging from 1 to 200, such as the product sold under the name 176-11187 (polycetylmethylsiloxane [$T_m$=32°–34° C.]) by the company GENERAL ELECTRIC;

polydimethylsiloxanes containing a mercapto functional group, of general formula:

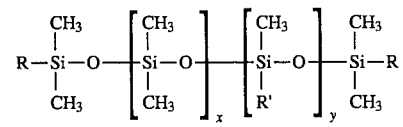

in which R and R' may represent, independently of one another, $CH_3$ or $(CH_2)_n$—SH, at least one of the radicals R and R' being $(CH_2)_n$—SH, n being greater than or equal to 3 and preferably less than 30,
x is an integer between 10 and 300, y is an integer between 1 and 40, such as the product sold under the name EXP-77 MERCAPTO FONCTIONAL SILICONE WAX by the company GENESEE (mercaptosilicone copolymer).

The silicone resins which can be used in the primary emulsion of the present invention may be chosen from trimethylsiloxysilicates of general formula:

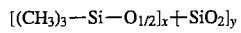

$[(CH_3)_3—Si—O_{1/2}]_x+SiO_2]_y$ amongst which may be mentioned the products sold under the name DC FLUID 593 by the company DOW CORNING, and the products called SILICONE SSX 4267, SILICONE SS 4230 and SILICONE SS 4267 sold by the company GENERAL ELECTRIC.

The non-silicone oils which can be used in the fatty phase of the primary emulsion of the present invention are chosen from fluid oils which are stable and pharmaceutically or cosmetically acceptable, and mixtures thereof.

These oils are chosen from vegetable or animal oils, modified or otherwise, such as sweet almond oil, avocado oil, castor oil, olive oil, jojoba oil, sunflower oil, wheatgerm oil, sesame oil, groundnut oil, raisinseed oil, soya oil, rapeseed oil, safflower oil, coconut oil, corn oil, hazelnut oil, shea butter, palm oil, apricot-kernel oil, calophyllum oil and purcellin oil; mineral oils such as, for example, liquid paraffin; synthetic oils and triglycerides of fatty acids, such as caprylic/capric triglycerides and $C_{10}$ to $C_{18}$ triglycerides.

The fatty phase of the primary W/O emulsion may additionally contain lipophilic additives which are conventionally used in cosmetics, for example sunscreens.

The aqueous phase of the primary W/O emulsion comprises water, a moisturizer such as glycerol, a polyol such as propylene glycol, hexylene glycol, dipropylene glycol or 1,3-butylene glycol, and an agent which stabilizes the emulsion, for example sodium chloride, magnesium dichloride and magnesium sulphate. It may also contain the conventional additives, such as preservatives, fragrances, dyes, active agents and sunscreens.

The Applicant has noted that the addition of compounds containing organofluorine chain members and hydrocarbon chain members to the primary W/O emulsion makes it possible to reduce the stickiness effect caused by the fatty-chain gelling agent present in the external aqueous phase, and also to increase the softness and unctuosity of the finished product.

These compounds containing organofluorine chain members and hydrocarbon chain members have a chemical structure which comprises a carbon skeleton in which some hydrogen atoms have been substituted by fluorine atoms, it being possible for the carbon skeleton to contain one or more heteroatoms and one or more organic functional groups.

For the compounds which contain organofluorine chain members and hydrocarbon chain members, the degree of substitution of hydrogen atoms by fluorine atoms is defined in the form of the ratio: number of atoms of fluorine/(number of atoms of fluorine+number of atoms of hydrogen), with only the hydrogen atoms which are linked to the carbon atoms of the skeleton being taken into account. The compounds which contain organofluorine chain members and hydrocarbon chain members and which are used in the emulsions according to the invention comprise at least one hydrocarbon group in the molecule.

These compounds which contain organofluorine chain members and which are used according to the invention preferably have a degree of substitution of between 0.5 and 95%. This degree of substitution is preferably greater than 10% and less than 80%.

The compounds which contain organofluorine chain members and hydrocarbon chain members and which are used according to the present invention have the following formula:

$$(R_F)_x\text{—}(A)_y\text{—}(R_H)_z$$

in which:
x represents 1, 2 or 3,
y represents 0 or 1,
z represents 0, 1, 2 or 3,
on condition that y and z are not simultaneously 0, and that, when z is 0, x is 2 or 3.

$R_F$ represents a fluorinated, saturated or unsaturated, aliphatic or aromatic radical having a linear, branched or cyclic chain, it being possible for this chain to be functionalized and/or to be interrupted by divalent atoms such as oxygen or sulphur, or trivalent atoms such as nitrogen, and/or substituted with hydrogen atoms or other halogen atoms, on condition that no more than one of these substituents which is different from fluorine is present for each two carbon atoms in the chain.

$R_H$ represents a saturated or unsaturated, aliphatic or aromatic hydrocarbon radical which has a linear, branched or cyclic chain, it being possible for this chain to be functionalized and/or interrupted by one or more divalent atoms such as oxygen or sulphur, or by one or more trivalent atoms such as nitrogen.

A represents a di-, tri- or quadrivalent radical such as:

$$\diagdown\!\!\!/\diagup \atop \diagup\!\!\!\!C\!\!\!\!\diagdown, \quad \diagup\!\!\!\!CH\text{—}, \quad \text{—}N\!\!\diagdown\diagup, \quad \text{—}CO\text{—}N\!\!\diagdown\diagup,$$

$$\text{—}SO_2N\!\!\diagdown\diagup, \quad \text{—}O\text{—}\underset{\underset{O}{|}}{\overset{\overset{O}{\|}}{P}}\text{—}O\text{—}$$

as well as the cyclic, aliphatic or aromatic structures comprising such a radical, or ethylenic unsaturations.

The expression "functionalized" refers, according to the invention, to internal, terminal or pendant substitution of the skeleton by at least one organic functional group, such as an alcohol, thiol, acid, carbonyl, sulphoxide, ester, amide, amine, phosphate, ethylenic, acetylenic, and enamine or sulphonamide functional group.

The term ethylenic unsaturation refers for example to:

$$\diagup\!\!\!\!C\!=\!C\!\!\!\!\diagdown, \quad \diagup\!\!\!\!C\!=\!CH\text{—} \quad \text{or} \quad \text{—}CH\!=\!CH\text{—}$$

$R_H$ preferably represents a $C_1$–$C_{22}$ linear or branched alkyl radical or a mixture of $C_1$–$C_{22}$ linear or branched alkyl radicals, a $C_6$–$C_{10}$ aryl radical or a $C_7$–$C_{15}$ aralkyl radical.

$R_F$ preferably represents a perfluoroalkyl radical having 4 to 22 carbon atoms.

By way of illustration it is possible to mention the compounds possessing perfluorocarbon groups and hydrocarbon groups, the total number of carbon atoms being between 10 and 30, the number of carbon atoms in the hydrocarbon groups being equal to or greater than twice the number of carbon atoms in the perfluoro carbon groups, as described in the document JP 63-002916.

Likewise, by way of illustration, it is possible to mention the organofluorine hydrocarbon compounds whose general structure is defined by the formula:

$$R_1\text{—}(CH_2)_n\text{—}X\text{—}[C_3H_5(OH)]\text{—}(Y)_x\text{—}R_2$$

in which $C_3H_5(OH)$ represents:

$$\text{—}CH_2\text{—}\underset{OH}{\underset{|}{CH}}\text{—}CH_2\text{—} \quad \text{or} \quad \text{—}\underset{CH_2OH}{\underset{|}{CH}}\text{—}CH_2\text{—} \quad \text{or}$$

$$\text{—}CH_2\text{—}\underset{CH_2OH}{\underset{|}{CH}}\text{—}$$

$R_1$ represents a perfluorinated, linear or branched $C_4$–$C_{20}$ alkyl radical, or a mixture of perfluorinated, linear or branched $C_4$–$C_{20}$ radicals, $R_2$ represents a linear or branched $C_1$–$C_{22}$ alkyl radical or a mixture of linear or branched $C_1$–$C_{22}$ alkyl radicals, or a $C_6$–$C_{10}$ aryl radical or a $C_7$–$C_{15}$ aralkyl radical, X and Y, which are identical or different, represent:

$$\text{—}O\text{—}, \quad \text{—}S\text{—}, \quad \overset{\overset{O}{\Uparrow}}{\text{—}S\text{—}}, \quad \text{or} \quad \overset{\overset{O\,\diagdown\!\!\diagup\,O}{\|\!\!\|}}{\text{—}S\text{—}} \ ;$$

with the proviso that X and Y do not simultaneously represent $$\overset{\overset{O}{\Uparrow}}{\text{—}S\text{—}} \quad \text{or} \quad \overset{\overset{O\,\diagdown\!\!\diagup\,O}{\|\!\!\|}}{\text{—}S\text{—}} \ ,$$

n is between 0 and 4, and
x represents 0 or 1.

These compounds used in accordance with the invention are described in FR-A 2,684,668 and EP-A-166,696.

It is also possible to use, moreover, according to the invention, the compounds of formula:

$$R_F\text{—}(CH_2)_n\text{—}X\text{—}[C_3H_5(OH)]\text{—}Y\text{—}(CH_2)_m\text{—}R'_F$$

in which $C_3H_5$ (OH) represents the structures:

$$\text{—}CH_2\text{—}\underset{OH}{\underset{|}{CH}}\text{—}CH_2\text{—} \quad \text{or} \quad \text{—}\underset{CH_2OH}{\underset{|}{CH}}\text{—}CH_2\text{—} \quad \text{or}$$

$$\text{—}CH_2\text{—}\underset{CH_2OH}{\underset{|}{CH}}\text{—}$$

$R_F$ and $R'_F$, which are identical or different represent a perfluorinated, linear or branched $C_4$–$C_{20}$ alkyl radical, or a mixture of perfluorinated, linear or branched $C_4$–$C_{20}$ alkyl radicals;

m and n, which are identical or different, represent 0, 1, 2, 3 or 4;

X and Y, which are identical, are —O— or —S—.

These compounds are described in DE-2,702,607, JP 89-193,236, JP 92-275,268 and U.S. Pat. No. 3,893,984.

It is also possible to use, in accordance with the invention, the compounds described in the document U.S. Pat. No. 3,952,066, of formula:

$$R_F\text{—}CH_2\text{—}CH_2\text{—}X\text{—}CH_2\text{—}\underset{Y}{\underset{|}{CH}}\text{—}Z$$

in which Y is OH, and Z is

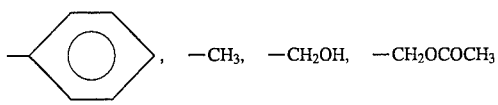

or else Y is —CH$_2$OH and Z is —O—COCH$_3$,
X represents

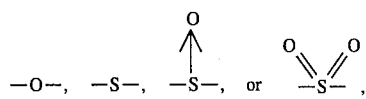

and
R$_F$ represents a perfluorinated, linear or branched, C$_4$–C$_{20}$ alkyl radical, or a mixture of perfluorinated, linear or branched, C$_4$–C$_{20}$ alkyl radicals;
or else the compounds described in the document DE 2,052,579, of formula:

R$_F$—CH=CH—CH$_2$—O—CH$_2$—[C$_2$H$_4$—OW]

in which
C$_2$H$_4$OW denotes:

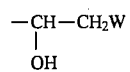 (a)

or

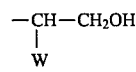 (b)

where W denotes:

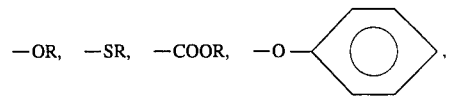,

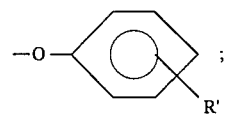;

R denotes a linear or branched C$_1$–C$_{18}$, alkyl radical,
R' denotes —CH$_3$ or —OH, in the ortho or para position, and
R$_F$ represents a perfluorinated, linear or branched, C$_4$–C$_{20}$ alkyl radical, or a mixture of perfluorinated, linear or branched, C$_4$–C$_{20}$ alkyl radicals.

According to a first embodiment of the invention, at least one silicone oil is used as fatty phase for the preparation of the primary W/O emulsion.

According to a second embodiment of the invention, a silicone oil of this kind is added as a dilution product to the primary W/O emulsion containing, as fatty phase, at least one silicone or non-silicone oil, immediately prior to the dispersion of the primary emulsion in the gelled external aqueous phase, in order to obtain the final, stable triple emulsion.

The triple emulsion of the present invention contains from 0.05 to 8% by weight of silicone-containing emulsifier, from 0.25 to 60% by weight of silicone oil, from 0 to 16% by weight of silicone gum, from 0 to 16% by weight of silicone wax, from 0 to 8% by weight of silicone resin, from 0 to 25% by weight of compound containing organofluorine and hydrocarbon chain members, from 0 to 50% by weight of glycols, from 0.1 to 3% by weight of fatty-chain gelling agent, from 0.1 to 3% by weight of neutralizing agent (triethanolamine, sodium hydroxide) and also the stabilizing agents for the primary emulsion, as indicated above, and, if appropriate, cosmetological or dermatological active substances, and also other adjuvants which are conventionally used in cosmetics, such as preservatives, dyes, fragrances, moisturizers, and sunscreens, the remainder being made up of water.

Yet another subject of the invention is the process for the preparation of a triple emulsion according to the invention.

According to a preferred embodiment of the process of the invention, in a first stage the primary water-in-oil emulsion is prepared by adding an aqueous phase to the fatty phase in order to obtain a W/O emulsion, the use of a maximum quantity of 10% by weight of silicone oil in the primary emulsion, calculated relative to the total weight of the triple emulsion, making it possible to prepare an emulsion which is stable at room temperature.

In a second stage it is possible, if appropriate, to dilute the primary emulsion thus obtained, before dispersing it in the gelled aqueous phase, with a silicone oil which may be identical to or different from that (those) used in the primary emulsion.

The primary emulsion is prepared so as to obtain a viscosity of the emulsion, in its dilute or undiluted form, which is between 0.1 Pa.s and 3 Pa.s, preferably between 0.13 Pa.s and 1.1 Pa.s.

In a third stage the triple emulsion is produced by adding the primary emulsion thus obtained, or the product diluted with a silicone oil, to a second, gelled aqueous phase which constitutes the external aqueous phase of the emulsion, so as to obtain a ratio R of proportions in the triple emulsion (TE) of the silicone-containing emulsifer and the primary emulsion (PE) and of the fatty-chain gelling agent in the external aqueous phase, which is between 0.1 and 1.75 and preferably between 0.2 and 1.2:

$$R = \frac{\% \text{ (g) of silicone-containing emulsifier in } EP}{\% \text{ (g) of fatty-chain gelling agent in the external aqueous phase}}$$

As already indicated above, the compositions in the form of a triple emulsion, in accordance with the invention, have particularly notable cosmetic properties, especially with regard to feel and appearance, which enables them to be used as bases for applying the cosmetic active substances to the skin.

The introduction of active substances into the internal and/or external aqueous phase and/or into the oily phase enables numerous uses of such a triple emulsion.

These emulsions may in particular be used in facial care products, for dry or greasy skin. In order to produce products for dry skin, water-soluble, moisturizing, active substances can be introduced into either of the two aqueous phases, such substances being, for example, glycerine, propylene glycol, sorbitol, proline, pyrrolidonecarboxylic acid and derivatives thereof, urea, hydrolysed collagen, aloe vera gel, hyaluronic acid and derivatives thereof, dimethylsilanol hyaluronate and allantoin.

Treatment products for greasy skin are obtained by introducing, into either of the two aqueous phases, water-soluble active substances such as provitamin B5, which is used as a emollient, or an antibacterial agent such as transthiolanediol 3,4-S-dioxide.

The emulsions according to the invention may also be used as make-up removing or facial cleansing products in the form of creams, milks or face-masks, for example, or as make-up products, by incorporation of fillers or pigments.

These emulsions may also be used as anti-sun products, by introduction of screening agents.

Examples of water-soluble sunscreen agents which can be used and which are capable of being introduced into the internal and/or external aqeous phase include 2-hydroxy-4-methoxybenzophenone-5-sulphonic acid, sold under the name UVINUL MS 40 by the company BASF. As lipid-soluble sunscreen agents for introduction into the oily phase, it is possible to use, for example, 2-ethylhexyl paramethoxycinamate [sic] sold under the name PARSOL MCX by the company GIVAUDAN or 2-hydroxy-4-methoxybenzophenone, sold under the name UVINUL M 40 by the company BASF.

The emulsions according to the invention may also be used in the preparation of after-sun products containing, for example, as soothing active agents, vitamin F and the moisturizers mentioned above.

Slimming products can also be obtained, by introducing water-soluble or lipid-soluble, slimming, active substances, respectively, into one of the two aqueous phases or into the fatty phase.

Water-soluble, slimming, active substances include xanthine derivatives such as caffeine, theobromine, theophylline, L-carnitine, dimethylaminoethyltheophylline hydrochloride, silicon derivatives of the methylsilanol theophylline acetate alginate type, or vegetable derivatives such as hydroglycolic extracts of English ivy, brown algae, or fresh wild pansy. Lipid-soluble, slimming, active substances include DL-alphatocopherol nicotinate, oily extract of ginseng root (Panax ginseng), oily extract of English ivy (Hedera Helix), oily extract of dry arnica flowers (Arnica Montana L), or oily extract of seaweed (Fucus Vesiculosus).

It is also possible to obtain body-care products, by introducing the abovementioned moisturizers and vegetable or mineral oils, and also hair products which are used, for example, to smooth down the hair, by introducing sunscreen agents in order to protect the hair from UV radiation.

The triple emulsions of the invention can also be used as products for heavy legs, containing as water-soluble active agents ginkgo biloba, melilot or ruscus, and conventional oils as emollients.

The following examples are intended to illustrate the invention without, moreover, being limiting in nature.

FORMULATION EXAMPLES

EXAMPLE 1

SLIMMING TRIPLE EMULSION

| PHASE A (W/O) | |
|---|---|
| * ABIL WE 09 ® | 0.5 g |
| (silicone surfactant containing 66.6% of AS) | |
| * DC QC F2 1671 ® (silicone gum) | 0.8 g |
| (DOW CORNING) | |
| * VOLATIL SILICONE 7158 ® (silicone oil) | 2.7 g |
| * Caffeine | 0.5 g |
| (PROLABO) | |
| - Sodium chloride | 0.16 g |
| * Glycerine | 0.4 g |
| * Propylene glycol | 4 g |
| - Preservatives, fragrances, dyes | qs |
| - Distilled water | 4 g |
| PHASE B | |
| * CARBOPOL 1342 ® | 0.3 g |
| (fatty-chain gelling agent) | |
| * CARBOPOL 980 ® (gelling agent) | 0.3 g |
| * Glycerine | 2 g |

-continued

| | | |
|---|---|---|
| * Propylene glycol | | 20 g |
| - Preservatives, dyes | qs | |
| * 99% Triethanolamine | | 0.6 g |
| - Distilled water | qs | 100 g |

$$R = \frac{0.5 \times 66.6\%}{0.3} = 1.1$$

* cf. appendix describing the raw materials

The triple emulsion is prepared by introducing phase A into phase B and ending by neutralization with triethanolamine.

A slimming cream is obtained which has a gelled, translucent appearance and can thus be massaged in.

EXAMPLE 2

TRIPLE EMULSION FOR THE HANDS

| PHASE A (W/O) | |
|---|---|
| * DC Q2 3225C ® | 5 g |
| (silicone surfactant containing 10% of AS) | |
| * DC FLUID 200 ® (silicone oil) | 0.4 g |
| (DOW CORNING) | |
| * DC FLUID 593 ® (silicone resin) | 1 g |
| (DOW CORNING) | |
| * Glycerine | 7 g |
| - Magnesium sulphate | 0.4 g |
| - Distilled water | 6.2 g |
| PHASE B | |
| * VOLATIL SILICONE 7158 ® | 10 g |
| (silicone oil) | |
| PHASE C | |
| * CARBOPOL 1342 ® | 0.3 g |
| (fatty-chain gelling agent) | |
| * CARBOPOL 980 ® (gelling agent) | 0.3 g |
| * NIPASTAT ® (preservatives) | 0.06 g |
| * Glycerine | 2 g |
| * GERMALL 115 ® | 0.2 g |
| * 99% Triethanolamine | 0.6 g |
| - Distilled water | qs 100 g |

$$R = \frac{0.5}{0.3} = 1.7$$

Phase A is diluted with Phase B and the mixture is then dispersed in Phase C in order to obtain the final triple emulsion.

A white cream-gel is obtained which is slightly translucent, smooth and shiny, and has moisturizing properties.

EXAMPLE 3

TRIPLE EMULSION FOR GREASY SKIN

| PHASE A (W/O) | |
|---|---|
| * ABIL WE 09 ® | 0.6 g |
| (silicone surfactant containing 66.6% of AS) | |
| * VISCASIL 60 M ® (silicone gum) | 0.2 g |
| (GENERAL ELECTRIC) | |
| * ABIL K 03 ® (silicone oil) | 1 g |
| (GOLDSCHMIDT) | |
| * DC FLUID 345 ® (silicone oil) | 3.4 g |
| * Glycerine | 2 g |
| - Magnesium sulphate | 0.2 g |
| - MEXORYL SN ® (antibacterial agent) | 0.5 g |
| (CHIMEX) | |
| - Distilled water | 11.1 g |

-continued

| PHASE B | | |
|---|---|---|
| * DC FLUID 345 ® (silicone oil) | | 5 g |
| PHASE C | | |
| * CARBOPOL 1342 ® (fatty-chain gelling agent) | | 0.6 g |
| * Glycerine | | 5 g |
| * Propylene glycol | | 10 g |
| - Preservatives, dyes | qs | |
| * 99% Triethanolamine | | 0.6 g |
| - Distilled water | qs | 100 g |

$$R = \frac{0.6 \times 66.6\%}{0.6} = 0.7$$

As in the preceding example, phase A is diluted with phase B and then the mixture is dispersed in phase C.

A translucent, non-greasy cream-gel is obtained which spreads and penetrates well, and is suited to greasy skin.

EXAMPLE 4

TINTED TRIPLE EMULSION FOR THE FACE

| PHASE A (W/O) | | |
|---|---|---|
| * ABIL WE 09 ® (silicone surfactant containing 66.6% of AS) | | 0.5 g |
| * DC FLUID 200 ® (silicone oil) | | 0.5 g |
| * VOLATIL SILICONE 7158 ® (silicone oil) | | 1.3 g |
| * DC Q2 1403 FLUID ® (silicone gum) | | 0.4 g |
| - Pigments | | 0.14 g |
| - Talc | | 0.2 g |
| * Glycerine | | 0.8 g |
| * Propylene glycol | | 1 g |
| - Polyethylene glycol | | 0.3 g |
| - Distilled water | | 4.86 g |
| PHASE B | | |
| * VOLATIL SILICONE 7158 ® (silicone oil) | | 15 g |
| PHASE C | | |
| * CARBOPOL 1342 ® (fatty-chain gelling agent | | 15 g |
| * 99% Triethanolamine | | 0.6 g |
| - Distilled water | qs | 100 g |

$$R = \frac{0.5 \times 66.6\%}{0.6} = 0.6$$

To prepare the triple emulsion the procedure of the preceding example is followed.

A gelled, tinted cream is obtained which is pleasant to apply.

EXAMPLE 5

ANTI-SUN TRIPLE EMULSION

| PHASE A (W/O) | | |
|---|---|---|
| * ABIL WE 09 ® (silicone surfactant containing 66.6% of AS) | | 0.8 g |
| * VOLATIL SILICONE 7158 ® (silicone oil) | | 2.8 g |
| * CB 185 ® (UV screen) (RHONE POULENC) | | 0.5 g |
| * ABIL AV 1000 ® (silicone oil) (GOLDSCHMIDT) | | 0.6 g |
| * ABIL WAX 2434 ® (silicone wax) | | 0.6 g |
| - VITAMIN E ACETATE | | 0.4 g |

-continued

| (HOFFMANN LAROCHE) | | |
|---|---|---|
| * Glycerine | | 0.4 g |
| * Propylene glycol | | 4 g |
| - Sodium chloride | | 0.16 g |
| - Preservatives, dyes | qs | |
| - Distilled water | qs | 100 g |
| PHASE B | | |
| * VOLATIL SILICONE 7158 ® (silicone oil) | | 10 g |
| PHASE C | | |
| * CARBOPOL 1342 ® (fatty-chain gelling agent) | | 0.8 g |
| * Propylene glycol | | 20 g |
| - Preservatives, fragrances | qs | |
| * 99% Triethanolamine | | 0.8 g |
| - Distilled water | qs | 100 g |

$$R = \frac{0.8 \times 66.6\%}{0.8} = 0.7$$

This triple emulsion is prepared by following a procedure like that of the preceding example.

A gelled, protective, anti-UV cream is obtained.

EXAMPLE 6

CONDITIONING COATING BALM TRIPLE EMULSION

| PHASE A (W/O) | | |
|---|---|---|
| * ABIL WE 09 ® (silicone surfactant containing 66.6% of AS) | | 0.8 g |
| * VOLATIL SILICONE 7158 ® (silicone oil) | | 2.8 g |
| * HUILE CL 1680 ® (silicone oil) (RHONE POULENC) | | 0.4 g |
| * VISCASIL 60 M ® (silicone gum) | | 0.2 g |
| - Sodium chloride | | 0.16 g |
| - Preservatives | qs | |
| * Glycerine | | 0.2 g |
| - Distilled water | qs | 100 g |
| PHASE B | | |
| * VOLATIL SILICONE 7158 ® (silicone oil) | | 5 g |
| PHASE C | | |
| * PEMULEN TR 1 ® (fatty-chain gelling agent) (GOODRICH) | | 1 g |
| * 99% Triethanolamine | | 1 g |
| - Distilled water | qs | 100 g |

$$R = \frac{0.8 \times 66.6\%}{1} = 0.5$$

The triple emulsion is prepared by following the procedure as in the preceding example.

A white gel is obtained which makes it possible to protect and coat the hair.

EXAMPLE 7

BODY GEL TRIPLE EMULSION

| PHASE A (W/O) | | |
|---|---|---|
| * ABIL WE 09 ® (silicone surfactant containing 66.6% of AS) | | 0.8 g |
| * VOLATIL SILICONE 7158 ® (silicone oil) | | 2.6 g |
| * FL 100/450 ® (fluorinated silicone oil) | | 1.4 g |

(SHIN ETSU)
- Fragrances   qs
- Sodium chloride   0.16 g
* Propylene glycol   4 g
* Glycerine   0.4 g
- Preservatives   qs
- Distilled water   10.64 g

PHASE B

* PEMULEN TR 1 ®   0.8 g
  (fatty-chain gelling agent)
- Butylene glycol   10 g
* Glycerine   5 g
* 99% Triethanolamine   0.8 g
- Preservatives, dyes   qs
- Distilled water   qs   100 g $$R = \frac{0.8 \times 66.6\%}{0.8} = 0.7$$

To prepare the triple emulsion, phase A is prepared and dispersed in phase B.

A translucent, unctuous and shiny cream-gel is obtained which is fresh on application and has moisturizing and emollient properties.

EXAMPLE 8

TRIPLE-EMULSION BODY GEL

PHASE A (W/O)

* ABIL WE 09 ®   0.6 g
  (silicone surfactant containing 66.6% of AS)
* VOLATIL SILICONE 7158 ® (silicone oil)   1.5 g
- 1-(2'-F-hexylethylthio)-3-(2"-ethyl-hexyloxy)-   1.5 g
  2-propanol
* Propylene glycol   3 g
- Sodium chloride   0.12 g
- Preservatives   0.03 g
- distilled water   8.25 g

PHASE B

* CARBOPOL 1342 ®   0.6 g
  (fatty-chain gelling agent)
* Propylene glycol   20 g
* Glycerine   3 g
- Preservatives, fragrances   0.26 g
* 99% Triethanolamine   0.2 g
- Distilled water   qs   100 g $$R = \frac{0.6 \times 66.6\%}{0.6} = 0.66$$

To prepare the triple emulsion, the procedure as in Example 1 is followed.

A smooth, translucent, shiny gel is obtained which is pleasant on application.

EXAMPLE 9

TRIPLE-EMULSION BODY GEL

PHASE A (W/O)

* ABIL WE 09 ®   0.8 g
  (silicone surfactant containing 66.6% of AS)
* VOLATIL SILICONE 7158 ® (silicone oil)   2 g
- 1-(2'-F-hexylethylthio)-3-(2"-ethyl-hexyloxy)-   2 g
  2-propanol
* Propylene glycol   4 g
- Sodium chloride   0.16 g
- Preservatives   0.04 g

- Distilled water   11 g

PHASE B

* CARBOPOL 1342 ®   0.6 g
  (fatty-chain gelling agent)
* Propylene glycol   20 g
* Glycerine   2 g
- Preservatives, fragrances   0.26 g
* 99% Triethanolamine   0.6 g
- Distilled water   qs   100 g $$R = \frac{0.8 \times 66.6\%}{0.6} = 0.88$$

To prepare the triple emulsion, the procedure as in Example 1 is followed.

A gelled composition is obtained which is translucent, shiny and pleasant on application.

EXAMPLE 10

TRIPLE EMULSION FOR THE BODY

PHASE A (W/O)

* ABIL WE 09 ®   1 g
  (silicone surfactant containing 66.6% of AS)
* VOLATIL SILICONE 7158 ® (silicone oil)   2.5 g
- 1-(2'-F-hexylethylthio)-3-(2"-ethyl-hexyloxy)-   2.5 g
  2-propanol
* Propylene glycol   5 g
- Sodium chloride   0.2 g
- Preservatives   0.05 g
- Distilled water   13.75 g

PHASE B

* CARBOPOL 1342 ®   0.6 g
  (fatty-chain gelling agent)
* Propylene glycol   20 g
* Glycerine   2 g
- Preservatives, fragrances   0.26 g
* 99% Triethanolamine   0.2 g
- Distilled water   qs   100 g $$R = \frac{1 \times 66.6\%}{0.6} = 1.1$$

To prepare the emulsion, the procedure as in Example 1 is followed.

A smooth gel is obtained which is translucent, shiny and pleasant on application.

EXAMPLE 11

TRIPLE EMULSION FOR THE FACE

PHASE A (W/O)

* Cetyl dimethicone copolyol,   0.45 g
  sold under the name ABIL EM90
  by the company GOLDSCHMIDT
  (silicone surfactant)
* Glycol distearate + tristearin,   0.075 g
  sold under the name UNITWIX by
  the company GUARDIAN
- 1-(2'-F-hexylethylthio)-3-(2"-ethyl-hexyloxy)-   3.6 g
  2-propanol
* Glycerine   0.75 g
- Magnesium sulphate   0.105 g
- Preservatives   0.045 g
- Distilled water   9.975 g -continued

PHASE B

| | | |
|---|---|---|
| * VOLATIL SILICONE 7158 ® (silicone oil) | | 6 g |
| PHASE C | | |
| * CARBOPOL 1342 ® | | 0.6 g |
| (fatty-chain gelling agent) | | |
| * Propylene glycol | | 20 g |
| * Glycerine | | 2 g |
| - Preservatives, fragrance | | 0.26 g |
| * 99% Triethanolamine | | 0.6 g |
| - Distilled water | qs | 100 g |

$$R = \frac{0.45}{0.6} = 0.75$$

To prepare the triple emulsion, the procedure as in Example 2 is followed.

A translucent gel is obtained which is pleasant on application.

EXAMPLE 12

TRIPLE EMULSION FOR THE FACE

PHASE A (W/O)

| | | |
|---|---|---|
| * Cetyl dimethicone copolyol, | | 0.6 g |
| sold under the name ABIL EM90 | | |
| by the company GOLDSCHMIDT | | |
| (silicone surfactant) | | |
| * Glycol distearate + tristearin, | | 0.1 g |
| sold under the name UNITWIX by | | |
| the company GUARDIAN | | |
| - 1-(2'-F-hexylethylthio)-3-(2''-ethyl-hexyloxy)- | | 4.8 g |
| 2-propanol | | |
| * Glycerine | | 1 g |
| - Magnesium sulphate | | 0.14 g |
| - Preservatives | | 0.06 g |
| - Distilled water | | 13.3 g |
| PHASE B | | |
| * VOLATIL SILICONE 7158 ® (silicone oil) | | 6 g |
| PHASE C | | |
| * CARBOPOL 1342 ® | | 0.6 g |
| (fatty-chain gelling agent) | | |
| * Propylene glycol | | 20 g |
| * Glycerine | | 2 g |
| - Preservatives, fragrance | | 0.26 g |
| * 99% Triethanolamine | | 0.6 g |
| - Distilled water | qs | 100 g |

$$R = \frac{0.6}{0.6} = 1$$

To prepare the triple emulsion, the procedure as in Example 2 is followed.

A translucent, unctuous gel is obtained.

APPENDIX—RAW MATERIALS

ABIL WE 09® GOLDSCHMIDT: Cetyl dimethicone copolyol, polyglyceryl-4 isostearate, hexyl laurate (33.3%/33.3%/33.4%)
VOLATIL SILICONE 7158® UNION CARBIDE: Cyclopentadimethylsiloxane
VISCASIL 60 M® GENERAL ELECTRIC: Polydimethylsiloxane
GERMALL 115® ISP: Imidazolidinylurea
PROPYLENE GLYCOL® DOW CHEMICAL: Propylene glycol
GLYCERINE PUR CODEX® STEARINERIE DUBOIS: Glycerine
CARBOPOL 980® GOODRICH: Carboxyvinyl polymer synthesized in a mixture of ethyl acetate/cyclohexane
99% TRIETHANOLAMINE® B.P.: Triethanolamine
SATIAGEL K 80® SANOFI: Pure carragheenan (D-galactopyranose sulphate)
KELTROL® KELCO: Xanthan/polysaccharides: glucose/mannose/glucuronic acid (40/30/30)
LUBRAJEL MS® GUARDIAN: Glyceryl polymethacrylate, glycerine, propylene glycol, water (3%/47%/1%/48.8%)
PURCELLIN LIQUIDE: Isopropyl myristate,
HUILE 2/066210 - cetearyl octanoate (10/90) DRAGOGO
CARBOPOL 1342® GOODRICH: Copolymer of acrylic acid/$C_{10}$–$C_{30}$ alkyl acrylate (CTFA name: acrylates/$C_{10}$–$C_{30}$ alkyl acrylate crosspolymer)
NIPASTAT® NIPA: Methylparaben, butylparaben, ethylparaben, propylparaben, isobutylparaben (57/15/14/7/7)
ABIL WAX 2434® GOLDSCHMIDT: Polystearoxy dimethylsiloxane
DC QC F2 - 1671® DOW CORNING: Dimethiconol/cyclomethicone (12.5%/87.5%)
CAFEINE® PROLABO: Caffeine
DC Q2 3225C® DOW CORNING: Ethoxylated polydimethylsiloxane, cyclomethicone (10/90)
DC FLUID 200® DOW CORNING: Polydimethylsiloxane
DC FLUID 593® DOW CORNING: Trimethylsiloxysilicate/polydimethylsiloxane (33%/67%)
ABIL K03® GOLDSCHMIDT: Polydimethylsiloxane
DC FLUID 345® DOW CORNING: Cyclopentadimethylsiloxane/cyclotetradimethylsiloxane (75/25)
MEXORYL SN® CHIMEX: Thiolanediol=transthiolanediol 3,4-S-dioxide
CB 185® RHONE POULENC: Copolymer of polydimethylsiloxane/benzylidenecamphor (silicone screening agent)
ABIL AV 1000® GOLDSCHMIDT: Polyphenyltrimethylsiloxane
HUILE CL 1680® RHONE POULENC: Monopentaerythritol trimethylsilyl/cyclotetradimethylsiloxane (50/50)
PEMULEN TR 1® GOODRICH: Copolymer of acrylic acid/$C_{10}$–$C_{30}$ alkyl acrylate (CTFA name: acrylates/$C_{10}$–$C_{30}$ alkyl acrylate crosspolymer)
FL 100/450® SHIN ETSU: Trifluoroalkyldimethylsiloxane
ABIL EM90® GOLDSCHMIDT: Cetyl dimethicone copolyol
UNITWIX GUARDIAN: Glycol distearate+tristearin (diester of ethylene glycol and stearic acid+triester of glycerol and stearic acid)

We claim:

1. Gelled triple water/silicone oil/water emulsion, characterized in that it comprises:

(A) a gelled, continuous, external aqueous phase which comprises at least one fatty-chain gelling agent of the $C_3$–$C_6$ monoethylenic carboxylic acid or anhydride/fatty-chain acrylic ester copolymer type;

(B) a silicone-containing fatty phase comprising at least one silicone oil and a silicone-containing emulsifier, forming the primary W/O emulsion with an aqueous phase.

2. Triple emulsion according to claim 1, characterized in that the gelled external aqueous phase additionally comprises another gelling agent chosen from carboxyvinyl polymers, glyceryl polymethacrylates, carragheenans and xanthan gums.

3. Triple emulsion according to claim 1, characterized in that the gelled external aqueous phase additionally contains glycols, neutralizing agents, preservatives, dyes, fragrances, active substances, sunscreens, moisturizers and unctuosity agents.

4. Triple emulsion according to claim 1 characterized in that the primary W/O emulsion contains at least one compound comprising organofluorine chain members and hydrocarbon chain members.

5. Triple emulsion according to claim 4, characterized in that the compound comprising organofluorine chain members and hydrocarbon chain members has a degree of substitution of between 0.5 and 95%.

6. Triple emulsion according to claim 1 characterized in that the fatty phase of the primary emulsion additionally comprises at least one silicone gum, one silicone wax and/or one silicone resin.

7. Triple emulsion according to claim 1 characterized in that the fatty phase of the primary emulsion additionally comprises non-silicone oils chosen from vegetable or animal oils, mineral or synthetic oils and fatty acid triglycerides, and also active substances and sunscreens.

8. Triple emulsion according to claim 1 characterized in that the aqueous phase of the primary emulsion comprises, besides water, salts which stabilize the emulsion, moisturizers, polyols, active substances, preservatives, sunscreens, fragrances and dyes.

9. Triple emulsion according to claim 1, characterized in that the viscosity of the primary emulsion is between 0.1 Pa.s and 3 Pa.s, preferably between 0.13 Pa.s and 1.1 Pa.s.

10. Triple emulsion according to claim 1 characterized in that the ratio of the proportions, in the triple emulsion, of the silicone-containing emulsifier of the primary emulsion to the fatty-chain gelling agent of the external aqueous phase is between 0.1 and 1.75 and preferably between 0.2 and 1.2.

11. Triple emulsion according to claim 1, characterized in that it comprises, relative to the total weight of the triple emulsion, from 0.05 to 8% of a silicone-containing emulsifier, from 0.25 to 60% of a silicone oil, from 0 to 16% of a silicone gum, from 0 to 16% of a silicone wax, from 0 to 8% of a silicone resin, from 0 to 25% by weight of compound containing organofluorine and hydrocarbon chain members, from 0.1 to 3% of a fatty-chain gelling agent, from 0.1 to 3% of a neutralizing agent, and from 0 to 50% by weight of glycol, and of salts chosen from sodium chloride, magnesium chloride and magnesium sulphate, in a quantity which is sufficient to stabilize the primary emulsion, and also, optionally, cosmetological or dermatological active substances, and any other adjuvant which is conventionally used in cosmetics, the remainder consisting of water.

12. Triple emulsion according to claim 1 characterized in that the silicone-containing emulsifier present in the primary W/O emulsion is chosen from dimethicone copolyols and preferably alkyl dimethicone copolyols.

13. Triple emulsion according to claim 1 characterized in that the silicone oil present in the primary W/O emulsion is chosen from cyclomethicones, polydimethylsiloxanes (dimethicones), polyphenyltrimethylsiloxanes (phenyl trimethicones), monopentaerythritol trimethylsilyl and fluorinated silicones such as polydimethylsiloxanes grafted with trifluoroalkyl groups.

14. Triple emulsion according to claim 1 characterized in that the silicone gum is chosen from polydimethylsiloxanes (dimethicones) of high molecular weight and polydimethylsiloxane-ols (dimethicone-ols).

15. Triple emulsion according to claim 1, characterized in that the silicone wax is chosen from alkoxypolydimethylsiloxanes (alkoxy dimethicones), alkylpolysiloxanes (alkyl dimethicones) and polydimethylsiloxanes having a mercapto functional group.

16. Triple emulsion according to claim 1 characterized in that the silicone resin is chosen from trimethylsiloxysilicates.

17. Process for the preparation of a triple emulsion according to claim 1, characterized in that, in a first stage, the primary W/O emulsion is prepared by adding an aqueous phase to a silicone-containing fatty phase and, in a second stage, the triple emulsion is prepared by addition of the primary emulsion obtained beforehand to a second, gelled, continuous, external aqueous phase, the primary emulsion containing not more than 10% by weight of silicone oil relative to the total weight of the final triple emulsion.

18. Process for the preparation of a triple emulsion according to claim 1, characterized in that, in a first stage, the primary W/O emulsion is prepared by adding an aqueous phase to a silicone-containing fatty phase comprising at least one silicone-containing emulsifier and a silicone or non-silicone oil, in a second stage the primary emulsion obtained is diluted with a silicone oil which is identical to or different from that (those) optionally used in the primary emulsion, and finally, in a third stage, the triple emulsion is prepared by addition of the diluted primary emulsion to a second, gelled, continuous, external aqueous phase.

19. Cosmetic composition for application to the skin or hair, characterized in that it comprises at least one triple emulsion as defined in claim 1.

20. Composition for use in dermatology and containing dermatologically active agents, characterized in that its vehicle consists of a triple emulsion as defined in claim 1.

* * * * *